US006200983B1

(12) United States Patent
El-Rashidy et al.

(10) Patent No.: US 6,200,983 B1
(45) Date of Patent: Mar. 13, 2001

(54) DOSAGE FORMS CONTAINING APOMORPHINE FOR AMELIORATING MALE ERECTILE DYSFUNCTION

(75) Inventors: Ragab El-Rashidy, Deerfield, IL (US); Jeremy P. W. Heaton, Gananoque (CA); Alvaro Morales, Kingston (CA); Michael A. Adams, Kingston (CA)

(73) Assignees: Pentech Pharmaceuticals, Inc., Buffalo Grove, IL (US); Queen's University at Kingston, Kingston (CA)

( * ) Notice: Subject to any disclaimer, the term of this patent is extended or adjusted under 35 U.S.C. 154(b) by 0 days.

(21) Appl. No.: 09/440,451

(22) Filed: Nov. 15, 1999

Related U.S. Application Data

(62) Division of application No. 09/102,235, filed on Jun. 22, 1998, now Pat. No. 5,985,889, which is a continuation of application No. 08/546,498, filed on Oct. 20, 1995, now Pat. No. 5,770,606, which is a continuation-in-part of application No. 08/231,250, filed on Apr. 22, 1994, now abandoned.

(51) Int. Cl.[7] .................................................. A61K 31/44
(52) U.S. Cl. ............................................................ 514/284
(58) Field of Search ................................................ 514/284

(56) References Cited

U.S. PATENT DOCUMENTS

| | | |
|---|---|---|
| 2,818,855 | 1/1958 | Miller . |
| 4,127,118 | 11/1978 | Latorre . |
| 4,521,421 | 6/1985 | Foreman . |
| 4,543,256 | 9/1985 | Neumeyer . |
| 4,687,773 | 8/1987 | Neumeyer et al. . |
| 4,727,064 * | 2/1988 | Pitha ........................ 514/58 |
| 4,801,587 | 1/1989 | Voss . |
| 5,242,391 | 9/1993 | Place et al. . |
| 5,270,323 | 12/1993 | Milne, Jr. et al. . |

FOREIGN PATENT DOCUMENTS

| | | |
|---|---|---|
| 0 579 435 | 1/1994 | (EP) . |
| WO-A-94 22445 | 10/1994 | (WO) . |

OTHER PUBLICATIONS

Tagliamonte et al., Pharm. Biochem. and Behavior 2:257 (1974).

Laudron et al., Biochem. Pharmacology 28:2161–2165 (1979).

Baldessarini et al., in Gessa et al., eds., *Apomorphine & Other Dopaminomimetics, vol. I: Basic Pharmacology*, Raven Press. N.Y. (1981), pp. 219–228.

Lal et al., J. Neural. Transmission 54:75–84 (1982).

Gower et al., European J. Pharmacolgy 122:239–244 (1986).

Segraves et al., Arch. Sexual Behav. 16(2):125–137 (1987).

Melis et al., Brain Research 415:98–104 (1987).

Lal, Prog. Neuro–Psychopharm. & Biol. Psych. 12:117–164 (1988).

Pehek et al., Pharm. Biochem. and Behavior 31:201–208 (1988).

Danjou et al., Br. J. Clin. Pharmac. 26:733–739 (1988).

Gancher et al., Ann. Neurol. 26:232–238 (1989).

Danjou et al., J. Pharmacol. Methods 21:61–69 (1989).

Segraves, Arch. Gen. Psych. 46:275–284 (1989).

Panegyres et al., Med. J. Australia 155:371–374 (1991).

Lal et al., J. Psych. Neurosci. 16(5):262–266 (1991).

Heaton et al., J. Urology 145:1099–1102 (1991).

Montastruc et al., Clin. Neuropharmacology 14(5):432–437 (1991).

Durif et al., Eur. J. Clin. Pharmacology 41:493–494 (1991).

Gancher et al., Movement Disorders 6(3):212–216 (1991).

Essink et al., J. Chromatography 570:419–424 (1991).

Segraves et al., J. Urology 145:1174–1175 (1991).

Durif et al., Clinical Neuropharmacology 16(2):157–166 (1993).

Seagraves, R.T., Dopamine agonists and their effect on the human penile erectile response, pp. 225–229 in Bancroft. J., editor, *The Pharmacology of Sexual Function and Dysfunction*, Excerpta Medica, Amsterdam (1995).

Lal et al., "Apomorphine–Induced Penile Tumescence in Impotent Patients –Preliminary Findings", Prog. Neuro–Psychopharmacol. & Biol. Psychiat. 11:235–242 (1987).

Lal et al., "Apomorphine: Clinical Studies on Erectile Impotence and Yawning", Prog. Neuro–Psychopharmacol. & Biol. Psychiat. 13:329–339 (1989).

* cited by examiner

*Primary Examiner*—William R. A. Jarvis
(74) *Attorney, Agent, or Firm*—Olson & Hierl, Ltd.

(57) ABSTRACT

Psychogenic impotence or erectile dysfunction can be identified in psychogenic male patients and can be ameliorated, without substantial undesirable side effects, by sublingual administration of apomorphine dosage forms so as to maintain a plasma concentration of apomorphine of no more than about 5.5 nanograms per milliliter.

3 Claims, 4 Drawing Sheets

DOSAGE FORMS CONTAINING APOMORPHINE FOR AMELIORATING MALE ERECTILE DYSFUNCTION

CROSS-REFERENCE TO RELATED APPLICATIONS

This application is a division of application Ser. No. 09/102,235, filed Jun. 22, 1998, now U.S. Pat. No. 5,985,889, which, in turn, is a continuation of application Ser. No. 08/546,498, filed Oct. 20, 1995, now U.S. Pat. No. 5,770,606, which is a continuation-in-part of application Ser. No. 08/231,250, filed Apr. 22, 1994, abandoned.

FIELD OF THE INVENTION

This invention, in one aspect, relates to dosage forms and methods for ameliorating erectile dysfunction in psychogenic male patients. In another aspect this invention relates to diagnosis of erectile dysfunction. More particularly, this invention relates to the use of apomorphine-containing compositions for amelioration of erectile dysfunction in psychogenic male patients and for diagnostic purposes.

BACKGROUND OF THE INVENTION

A normal erection occurs as a result of a coordinated vascular event in the penis. This is usually triggered neurally and consists of vasodilation and smooth muscle relaxation in the penis and its supplying arterial vessels. Arterial inflow causes enlargement of the substance of the corpora cavernosa. Venous outflow is trapped by this enlargement, permitting sustained high blood pressures in the penis sufficient to cause rigidity. Muscles in the perineum also assist in creating and maintaining penile rigidity. Erection may be induced centrally in the nervous system by sexual thoughts or fantasy, and is usually reinforced locally by reflex mechanisms. Erectile mechanics are substantially similar in the female for the clitoris.

Impotence or male erectile dysfunction is defined as the inability to achieve and sustain an erection sufficient for intercourse. Impotence in any given case can result from psychological disturbances (psychogenic), from physiological abnormalities in general (organic), from neurological disturbances (neurogenic), hormonal deficiencies (endocrine) or from a combination of the foregoing.

These descriptions are not exact, however. There is currently no standardized method of diagnosis or treatment. As used herein, psychogenic impotence is defined as functional impotence with no apparent overwhelming organic basis. It may be characterized by an ability to have an erection in response to some stimuli (e.g., masturbation, spontaneous nocturnal, spontaneous early morning, video erotica, etc.) but not others (e.g., partner or spousal attention).

Various methods for the treatment of impotence have been suggested, including external devices, for example, tourniquets (see U.S. Pat. No. 2,818,855). In addition, penile implants, such as hinged or solid rods and inflatable, spring driven or hydraulic models, have been used for some time. The administration of erection effecting and enhancing drugs is taught in U.S. Pat. No. 4,127,118 to LaTorre. That patent teaches a method of treating male impotence by injecting into the penis an appropriate vasodilator, in particular, an adrenergic blocking agent or a smooth muscle relaxant to effect and enhance an erection. More recently, U.S. Pat. No. 4,801,587 to Voss et al. teaches the application of an ointment to relieve impotence. The ointment consists of the vasodilators papaverine, hydralazine, sodium nitroprusside, phenoxybenzamine, or phentolamine and a carrier to assist absorption of the primary agent through the skin. U.S. Pat. No. 5,256,652 to El-Rashidy teaches the use of an aqueous topical composition of a vasodilator such as papaverine together with hydroxypropyl-β-cyclodextrin.

Recently the effect of apomorphine on penile tumescence in male patients afflicted with psychogenic impotence has been studied. These studies show that while apomorphine can indeed induce an erection in a psychogenic male patient, the apomorphine dose required to achieve a significant erectile response is usually accompanied by nausea or other serious undesirable side effects such as hypertension, flushing and diaphoresis. The specific mechanisms by which apomorphine acts to produce an erectile response in a human patient are not yet completely understood, however.

Moreover, apomorphine has been shown to have very poor oral bioavailability. See, for example, Baldessarini et al., in Gessa et al., eds., *Apomorphine and Other Dopaminomimetics, Basic Pharmacology*, Vol. 1, Raven Press, N.Y. (1981), pp. 219–228.

Thus the search is continuing for an effective treatment of psychogenic impotence in male patients as well as for diagnostic methods that can identify such patients. It has now been found that certain delivery systems for apomorphine can provide a practical therapeutic and/or diagnostic "window" while reducing the likelihood of undesirable side effects.

SUMMARY OF THE INVENTION

It has now been found that, for an optimal erectile response, steady state circulating serum and mid-brain tissue levels of apomorphine are to be maintained within a relatively closely defined range.

Sublingual apomorphine dosage forms, usually containing about 2.5 to about 10 milligrams of apomorphine, have been found to be effective in male patients suffering from psychogenic erectile dysfunction for the induction and maintenance of an erection sufficient for intercourse (i.e., vaginal penetration) without nausea or other undesirable side effects. The apomorphine is administered sublingually, preferably about 15 to about 20 minutes prior to sexual activity, and so as to maintain a predetermined circulating serum levels and mid-brain tissue levels of apomorphine during the period of sexual activity sufficient to induce an erection adequate for vaginal penetration but less than the amount that induces nausea. The plasma concentration of apomorphine should be maintained at no more than about 5.5 nanograms per milliliter, preferably about 0.3 to about 4 nanograms per milliliter, and more preferably about 1 to about 2 nanograms per milliliter.

The foregoing sublingual apomorphine dosage forms are also suitable for screening patients complaining of erectile dysfunction so as to identify patients of psychogenic etiology.

DETAILED DESCRIPTION OF PREFERRED EMBODIMENTS

Figure 1:
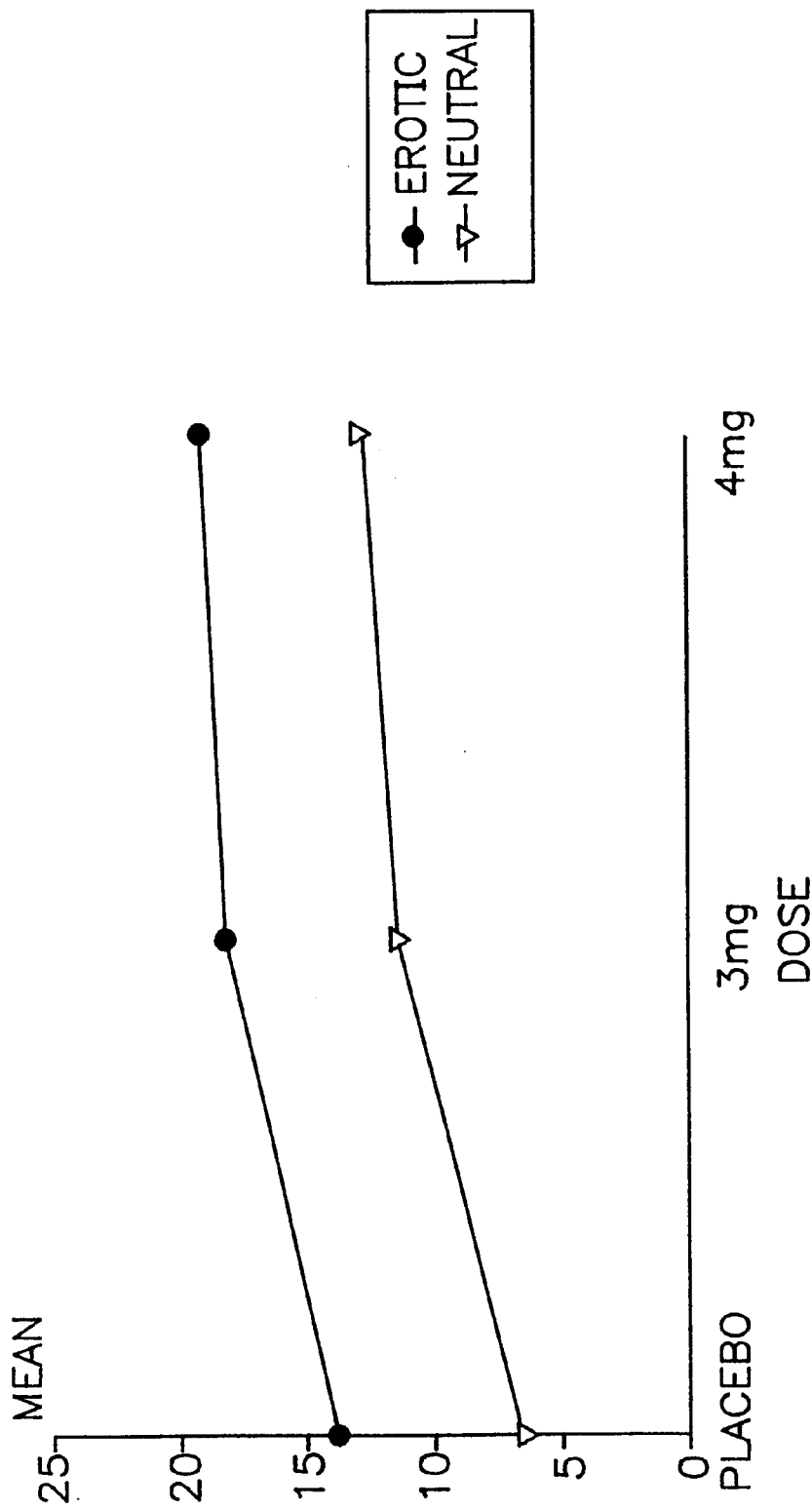
FIG. 1 is a graphical representation of mean erectile function, expressed as RIGISCAN™ monitor value, as a function of apomorphine dose.

Apomorphine is a dopamine receptor agonist that has a recognized use as an emetic when administered subcutaneously in about a 5-milligram dose. For the purposes of the present invention, apomorphine or a similarly acting dopamine receptor agonist is administered in an amount sufficient to excite cells in the mid-brain region of the patient but with minimal side effects. This cell excitation is believed to be part of a cascade of stimulation that is likely to include neurotransmission with serotonin and oxytocin.

The dopamine receptors in the mid-brain region of a patient can be stimulated to a degree sufficient to cause an erection by the sublingual administration of apomorphine so as to maintain a plasma concentration of apomorphine of no more than about 5.5 nanograms per milliliter (5.5 ng/ml). The sublingual administration usually takes place over a time period in the range of about 2 to about 10 minutes, or longer. The amount of apomorphine administered sublingually over this time period preferably is in the range of about 25 micrograms per kilogram ($\mu g/kg$) of body weight to about 60 $\mu g/kg$ of body weight.

The apomorphine is administered preferably about 15 to about 20 minutes prior to sexual activity.

Apomorphine can be represented by the formula

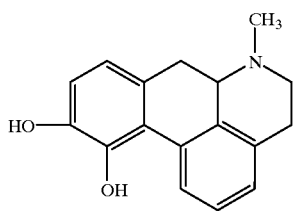

and exists in a free base form or as an acid addition salt. For the purposes of the present invention apomorphine hydrochloride is preferred; however, other pharmacologically acceptable moieties thereof can be utilized as well. The term "apomorphine" as used herein includes the free base form of this compound as well as the pharmacologically acceptable acid addition salts thereof. In addition to the hydrochloride salt, other acceptable acid addition salts are the hydrobromide, the hydroiodide, the bisulfate, the phosphate, the acid phosphate, the lactate, the citrate, the tartarate, the salicylate, the succinate, the maleate, the gluconate, and the like.

Illustrative preferred sublingual dosage forms are set forth in Table I, below.

TABLE I

150-Milligram Apomorphine Hydrochloride Sublingual Tablets

| 3-mg Tablet | |
| --- | --- |
| Apomorphine Hydrochloride | 2.00 wt-% |
| Mannitol | 66.67 wt-% |
| Ascorbic Acid | 3.33 wt-% |
| Citric Acid | 2.00 wt-% |
| Avicel PH102 | 15.00 wt-% |
| Methocel E4M | 10.00 wt-% |
| Aspartame | 0.67 wt-% |
| Magnesium Stearate | 0.33 wt-% |
| 4-mg Tablet | |
| Apomorphine Hydrochloride | 2.66 wt-% |
| Mannitol | 66.00 wt-% |
| Ascorbic Acid | 3.33 wt-% |
| Citric Acid | 2.00 wt-% |
| Avicel PH102 | 15.00 wt-% |
| Methocel E4M | 10.00 wt-% |
| Aspartame | 0.67 wt-% |
| Magnesium Stearate | 0.33 wt-% |
| 5-mg Tablet | |
| Apomorphine Hydrochloride | 3.33 wt-% |
| Mannitol | 65.34 wt-% |
| Ascorbic Acid | 3.33 wt-% |
| Citric Acid | 2.00 wt-% |
| Avicel PH102 | 15.00 wt-% |
| Methocel E4M | 10.00 wt-% |
| Aspartame | 0.67 wt-% |
| Magnesium Stearate | 0.33 wt-% |

If desired, and in order to facilitate absorption and thus bioavailability, the presently contemplated dosage forms can also contain, in addition to tabletting excipients, β-cyclodextrin or a β-cyclodextrin derivative such as hydroxypropyl-β-cyclodextrin (HPBCD). Illustrative dosage forms containing HPBCD are shown in Tables II and III, below.

TABLE II

Apomorphine Hydrochloride Sublingual Tablets With Hydroxypropyl-β-Cyclodextrin

| | mg/Tab |
| --- | --- |
| Apomorphine Hydrochloride | 4.0 |
| HPBCD | 5.0 |
| Ascorbic Acid | 10.0 |
| PEG8000 | 39.5 |
| Mannitol | 39.5 |
| Aspartame | 2.0 |
| TOTAL | 100.0 |

TABLE III

Apomorphine Hydrochloride Sublingual Tablets With β-Cyclodextrin

|  | mg/Tab |
| --- | --- |
| Apomorphine Hydrochloride | 5.0 |
| β-Cyclodextrin | 20.0 |
| Ascorbic Acid | 5.0 |
| Mannitol | 68.9 |
| Magnesium Stearate | 1.0 |
| D&C Yellow 10 Aluminum Lake | 0.1 |
| TOTAL | 100.0 |

The onset of nausea can be obviated or delayed by delivering apomorphine at a controlled dissolution rate so as to provide circulating serum levels and mid-brain tissue levels of apomorphine sufficient for an erection without inducing nausea. When apomorphine is administered at or near the relatively higher amounts of the aforementioned dosage range, the likelihood of nausea onset can be reduced by concurrent administration of a ganglionic agent (inhibitor of ganglionic response) such as nicotine or lobeline sulfate. For this purpose, the weight ratio of apomorphine to ganglionic agent is in the range of about 10 to about 1.

Other antiemetic agents that can be used in conjunction with apomorphine are antidopaminergic agents such as metoclopramide, and the phenothiazines, e.g., chlorpromazine, prochlorperazine, pipamazine, thiethylperazine, oxypendyl hydrochloride, and the like. Also suitable are the serotonin (5-hydroxytryptamine or 5-HT) antagonists such as domperidone, odansetron (commercially available as the hydrochloride salt under the designation Zofran®), and the like, the histamine antagonists such as buclizine hydrochloride, cyclizine hydrochloride, dimenhydrinate (Dramamine), and the like, the parasympathetic depressants such as scopolamine, and the like, as well as other anti-emetics such as metopimazine, trimethobenzamide, benzquinamine hydrochloride, diphenidol hydrochloride, and the like.

Nicotine-containing dosage forms and domperidone-containing dosage forms are illustrated in Table IV, below.

TABLE IV

Apomorphine Hydrochloride Sublingual Tablets Containing an Anti-Emetic Agent

|  | mg/Tab |
| --- | --- |
| Apomorphine Hydrochloride | 5.0 |
| Ascorbic Acid | 5.0 |
| Mannitol | 67.9 |
| Magnesium Stearate | 1.0 |
| Nicotine | 1.0 |
| β-Cyclodextrin | 20.0 |
| D&C Yellow 10 Aluminum Lake | 0.1 |
| TOTAL | 100.0 |
| Apomorphine Hydrochloride | 5.0 |
| Ascorbic Acid | 5.0 |
| Mannitol | 58.9 |
| Magnesium Stearate | 1.0 |
| Domperidone | 10.0 |
| β-Cyclodextrin | 20.0 |
| D&C Yellow 10 Aluminum Lake | 0.1 |
| TOTAL | 100.0 |

The preferred sublingual dosage forms dissolve within a time period of at least about 2 minutes but less than about 10 minutes. The dissolution time can be longer, however, if desired as long as the necessary plasma concentration of apomorphine can be maintained. More preferably, the dissolution time in water for the presently contemplated dosage forms is about 3 minutes to about 5 minutes.

The present invention is illustrated further by the following studies which were focused on two specific objectives. The first was to determine whether, relative to placebo response, patients who presented with "psychogenic" impotence (i.e., patients who were still capable of achieving erections) demonstrated improved erectile function and/or enhanced sexual desire post-dosing with sublingual apomorphine (APO). The second objective was to determine what dose(s) of various forms of sublingual APO are effective in this group of patients for inducing an erection that is sufficient for vaginal penetration.

Participating patients were selected from among those that initially presented with the complaint of impotence. These patients underwent a thorough urological assessment by a urologist as well as an assessment by a psychiatrist. Diagnostic testing for erectile difficulties was extensive and included the following: biochemical profile, nocturnal penile tumescence (NPT) monitoring, doppler flow studies, biothesiometry, corporal calibration testing with an intracorporal injection of triple therapy and dynamic cavernosometry. These tests were used to rule out any arterial, venous or peripheral neural causality of impotence. Any patients with abnormalities in any of these three areas were excluded from entry to the trials. The inclusion/exclusion criteria for all four pilot studies are set forth in Table V, below. Patients who met all criteria were diagnosed as having impotence primarily of a psychogenic origin. If there were no known medical contraindications to the use of a dopaminergic medication they were offered entry into an APO trial.

Instructions were given regarding the protocol by the research clinician, and an informed consent was obtained. Patients were advised that they were free to withdraw from the trial at any time without penalty or prejudice. They were tested on at least three separate days at three separate doses (placebo and two active medication doses) with an interval of no less than three days between. The experimental scheme described below was used in all four pilot studies.

Patients were seated in a comfortable chair and a RIGISCAN™ ambulatory tumescence monitor (Dacomed Corp., Minneapolis, Minn.) was placed on the patient and the computer was set in the real time monitoring mode. Blood pressure and heart rate were recorded pre-dosing with APO or placebo and at the end of the testing session. Visual analogue scales (VAS) were completed by the patient pre-dosing as well as post-dosing (at the end of the testing session). These scales reflected the patient's sense of well being, level of sedation, tranquilization, anxiousness, arousal and any changes in yawning behavior. In a single-blind fashion, apomorphine or placebo was administered to the patient sublingually. Doses of active medication varied on the formulation of the apomorphine administered (liquid or tablet). Because of the possibility of nausea and the tolerance to this effect that prior dosing conveys, the patient was given increasing doses at each testing. However, the patient was unaware of the dose that he was receiving (single-blind). Patients were instructed not to swallow the medication, but to keep it under their tongue and allow it to be absorbed there.

Symptoms as they were volunteered were recorded by the research clinician. If the patient complained of nausea or felt unwell in any way he was asked if he wanted to abort the trial. If the trial was aborted, the patient was given Gravol 50 mg p.o. at that time. The patient was monitored by the research clinician until these side-effects had subsided. He was asked to return the following week for retesting at the same dose and was instructed to begin treatment with Domperidone 10 m.g. p.o. TID the day before and morning of his next session.

Patients not experiencing nausea or any other significant adverse effects within fifteen minutes post-dosing with APO or placebo viewed segments of standardized erotic videos to provide sexual stimulation. The following sequence of videos was viewed: a ten minute erotic video, a neutral video lasting between five and ten minutes in duration and finally another ten minute erotic video. The duration of the testing session for each dose level lasted between 45 and 60 minutes. After determining the most effective dose of apomorphine for the patient, he was then offered APO for domestic trial at that dose.

Results of Pilot Studies 1 to 4

The frequency and the magnitude of erectile responses were documented with each dose of apomorphine or placebo. Data obtained from the RIGISCAN™ monitor was downloaded and each session was scanned. Erection responses were then scored for rigidity (%) and tumescence (cm.) at both the tip and base of the penis and an overall score was given that corresponded to these parameters during the viewing of both erotic and neutral video segments (see Table VI, below). A score of less than 16 indicated erectile dysfunction and a poor response to apomorphine at that dose.

Visual analogue scales (See Table IX) were compared both pre- and post-dosing, and examined for changes in feeling of well being, levels of arousal, anxiousness, sedation/tranquilization and yawning behavior. Blood pressure and heart rate were also compared pre- and post-dosing.

Effects of apomorphine that were both reported to and observed by the research clinician were grouped into two categories: Adverse Effects (i.e., flushing, diaphoresis, nausea, vomiting, changes in blood pressure or heart rate) or Primary Effects (i.e., yawning and erections).

Each pilot study was reviewed under the categories mentioned above.

Pilot Study #1

The initial formulation evaluated was liquid apomorphine administered via sublingual route. APO was prepared by a clinic pharmacist and dissolved in a solution of sodium metabisulfite and ethylenediamine tetraacetic acid (EDTA). The final concentration was 100 mg/ml. Patients were tested on three separate occasions at three separate doses (placebo; 10 mg; 20 mg)

Twelve patients entered into this trial. All patients had reported erectile dysfunction greater than 1 year in duration. The age range in this group was from 38 to 60 years. One patient withdrew after placebo and another withdrew after adverse effects at the 20 mg dose. That left a total evaluable group of ten. All ten patients had previously received yohimbine HCl for erectile dysfunction. Eight had failed a trial of yohimbine HCl. Of this group of eight, 6 were successful with apomorphine.

Seven (70%) were success (score of no less than 16 on both neutral and erotic video segments; Table VI) and three (30%) were categorized as failures with apomorphine. Six out of the seven successful patients continued on with a domestic trial of apomorphine at the dose that gave them the best response during testing. Three required treatment with Domperidone the day before and morning of apomorphine usage. The range of domestic use varied from two to seven months.

Analysis of visual analogue scales pre- and post-dosing with apomorphine indicated the following. At the end of the session patients were relaxed but not sedated. There was no evidence of arousal or anxiousness. Yawning behavior changes were evident on these scales with the incidence of yawning increasing between 15 and fifty minutes post-dosing and with each increase in dosing. Each patient experienced between two to five yawns per session. These changes were not evident with placebo.

The primary effect of yawning was both reported by patients and observed at both 10 mg and 20 mg doses. No yawning was reported with placebo. Adverse effects were reported at both dose levels. Two patients who did not experience nausea or diaphoresis were researched for similarities in their patient profiles but none were found. Anywhere from ten to fifteen minutes post-dosing the other eight patients developed sudden onset of various levels of nausea (and in one instance vomiting), diaphoresis, dizziness, double or blurred vision, decrease in both blood pressure and heart rate and pale or ashen coloring. Side effects varied from being transient and brief to lasting as long as from 30 to 40 minutes. One patient reported a stuffy nose starting approximately 30 minutes post-dosing and lasting for approximately 10 minutes. No adverse effects were reported post placebo dosing.

The foregoing Pilot Study leads to the following conclusions:

1. Apomorphine is effective in inducing erectile episodes without increasing libido in the "psychogenically" impotent male.
2. Both 10 mg and 20 mg doses produce erectile responses.
3. Both doses produced adverse effects (nausea, vomiting, diaphoresis, etc.) that would be unacceptable to patients and their partners, however. These effects can be counteracted with the use of Domperidone.

Pilot Study #2

The first sublingual tablet formulations evaluated were 2.5 and 5 mg. Patients were tested on three separate occasions at three separate doses (placebo; 2.5 mg, 5 mg).

A total of eight patients entered into this trial. All patients reported erectile difficulties for more that two years. The age range was from 38 to 62 years. All had failed a trial of yohimbine HCl. One patient withdrew from the trial after experiencing adverse effects at the 5 mg dose. That left a total of seven evaluable patients.

Two (29%) were successes (score of no less than 16; Table VI) and five (71%) were failures during lab testing. The two successful patients went onto a domestic trial of apomorphine at the 2.5 mg dose which was the most effective and did not produce adverse effects. Both patients used apomorphine at home for no less than two months with satisfactory results.

Analysis of visual analogue scales pre- and post-dosing with apomorphine indicated the same trends as with the liquid apomorphine preparation. Patients were relaxed but not sedated. No evidence of arousal or anxiousness was noted.

The primary effect of yawning was both reported by patients and observed at both 2.5 mg and 5 mg doses. The incidence of yawning increased between fifteen and forty minutes post-dosing. At the 2.5 mg dose all patients who failed testing had only one or two yawns per session. The 5 mg dose not only produced adverse effects (nausea, diaphoresis, dizziness, blurred vision, facial flushing, drop in both heart rate and blood pressure) but also increased yawning responses to three to five times per session. The two successful patients experienced three to five yawns at both the 2.5 mg and 5 mg doses. These changes were not evident with placebo.

At the end of Pilot Study #2 the following conclusions were made:

1. There appears to be a correlation between the effectiveness of the dose and yawning response (poor responders experience less yawning).
2. Both 2.5 and 5 mg doses produced erectile responses in some patients. The apparent 28% success rate was because of lab use only (failures were not given drug to take home) and lack of available intermediate doses.
3. In some instances the 5 mg dose can produce adverse effects (i.e., nausea, diaphoresis, etc.) that may be unacceptable to patients and their partners. These effects can be counteracted with the administration of Domperidone or nicotine (e.g., by smoking).
4. The sublingual tablets were easy to administer and dissolved within five minutes.

Pilot Study #3

Apomorphine was evaluated as an aqueous intranasal spray (1.25 mg per puff). The first patient was an anxious, 53 year old male who had been experiencing erectile dysfunction for two years. This patient had previously failed a trial of yohimbine.

He was tested on three separate occasions at three separate doses (placebo, 2.5 mg; 3.75 mg) and was categorized as a failure with the score of less than sixteen on both erotic and neutral video segments. He experienced yawning with both 2.5 mg and the 3.75 mg and was successful with this trial for two months until he inadvertently increased the dose. Adverse effects occurred within five minutes post-dosing (nausea and vomiting, dizziness, double and blurred vision, diaphoresis, and ashen coloring). The patient refused to retry medication after this incident. He stated he did not like this formulation.

Patient No. 2 was twenty-one year old male with erectile problems of a duration of three years. He had failed a previous course of yohimbine HCl. Ten minutes post-dosing with apomorphine at 2.5 mg he experienced yawing for a total of five yawns, and then experienced immediately major hemodynamic adverse effects. These included pale and ashen coloring, diaphoresis, nausea and vomiting, blurred vision, hypotension with a blood pressure of 70/50. Twenty minutes post adverse effect, vital signs were stable. The patient was feeling well, and coloring was good. This patient was then dropped from further testing.

Although the intranasal administration was effective in eliciting an erection, further testing of this intranasal formulation of apomorphine was discontinued because of possible overdose and increased side effects. The foregoing experience illustrates the need for reliable and relatively safer dosage forms, however.

Pilot Study #4

New sublingual tablet formulations of apomorphine at 3, 4 and 5 mg doses (Table I, above) were evaluated. Patients were tested on at least three separate occasions on at least three separate doses (placebo; 3 mg; and 4 mg). A 5 mg sublingual dose was also tested in some patients. The results of this study are summarized in Tables VII and VIII A–C, below.

To date, twelve patients have been completely evaluated on this formulation. All patients reported erectile dysfunction for more than two years. The patients' age range was thirty-nine to sixty-six years. Three patients had been successful with yohimbine HCl in the past, and two had previously not tried this compound. Seven patients of this group of twelve had previously failed a trial of yohimbine HCl. Of this latter group of seven, four were successfully treated with apomorphine.

Eight (67%) have been successful with apomorphine to date. Four (33%) were failures with apomorphine. Both 3 mg and 4 mg doses produced erectile responses. Several patients went on to a trial of the 5 mg sublingual dose which did not appear to be more effective than the relatively lesser doses in terms of erectile response. All eight of the successful patients continued on with the domestic use for a time period of one to four months. All patients reported good erectile activity and no side effects.

Analysis of visual analogue scales, both pre- and post-dosing with apomorphine, again indicated that the patients were relaxed but not sedated, and did not have feelings of arousal or anxiousness post-dosing. The new formulations tested (3 mg; 4 mg; and 5 mg) were devoid of adverse effects. The patients felt well post testing, and did not report or demonstrate any adverse effects that had traditionally been seen with the administration of previous apomorphine liquid and intranasal preparations (Pilot Studies No. 1 and No. 3). The primary effect of yawning was still reported and observed at all doses, but the number and frequency of yawns was small (one or two).

The foregoing pilot study shows that 3-mg, 4-mg and 5-mg apomorphine doses are effective in inducing penile erections, and also that there are no serious adverse effects with these preparations. Domestic use of these preparations was well accepted by patients and their partners. They were content with the convenience of dosing approximately fifteen minutes prior to sexual activity. All patients have stated that this was more acceptable than dealing with dosing on a routine basis.

TABLE V

Inclusion/Exclusion Criteria

INCLUSION CRITERIA:
1. Age 18–66 years.
2. NPT circumference increase of 1.5 cm or more on one night and >70% rigidity.
3. ICI circumference increase of 1.5 cm or more and >70% rigidity.

EXCLUSION CRITERIA:
1. Currently severe or life threatening systemic disease.
2. Clinically significant ECG abnormalities.
3. Personal or first degree family history of epilepsy.
4. Abnormal: Hepatic/renal function Hematology
5. Low: pre-trial testosterone
   Low or High: LH
   High: Prolactin
6. Hypertension requiring treatment.
7. History of depression requiring treatment with antidepressants, ECT, or hospitalization.
8. Symptomatic ischemic heart disease/or MI within the last three months.
9. Diabetes.
10. Failure to obtain informed consent.
11. Legal cases.
12. Unable or unwilling to comply with protocol.
13. Drinks more than (on average) 45 units alcohol per week/or uses illicit drugs.
14. History of syncope.
15. Prohibited Drugs: sympathetic or parasympathetic types drugs, Beta blockers, Vasodilators, psychotropic medications, tranquilizers, thiazides, Captopril, Verapmil, Furosemide, Spironolactone, Metochlopramide, Cimetidine or other drugs which are likely to influence erectile function.

TABLE VI

Response to Erotic Videotape

1. Maximum increase in penile circumference

| Circumference (cms.) | | Score |
|---|---|---|
| 0–<0.5 cm. | | 0 |
| 0.5–<1.0 cm. | | 1 |
| 1.0–<1.5 cm. | | 2 |
| 1.5–<2.0 cm. | | 3 |
| 2.0–<2.5 cm. | lasts <1 min. | 4 |
| 2.5 or more | lasts <1 min. | 5 |
| 2.0–<2.5 cm. | lasts at least 1 min. | 6 |
| 2.5 or more | lasts at least 1 min. | 7 |
| 3.0 or more | lasts at least 5 min. | 8 |
| 3.0 or more | lasts at least 10 min. | 9 |

A. Maximum increase in penile tip circumference _____ Score
B. Maximum increase in penile basal circumference _____

2. Maximum penile rigidity

| Rigidity (%) | Score |
|---|---|
| 0–<10 | 0 |
| 10–<20 | 1 |
| 20–<30 | 2 |
| 30–<40 | 3 |
| 40–<50 | 4 |
| 50–<60 | 5 |
| 60–<70 | 6 |
| 70–<80 | 7 |
| 80–<90 | 8 |
| 90–100 | 9 |

C. Maximum penile tip rigidity _____ Score
D. Maximum penile basal rigidity _____

3. Total score (A, B, C & D) _____ _____

A score of less than 16 indicates erectile dysfunction

TABLE VII

Summary of Results from Pilot Study #4 in Psychogenic Patients

| | | PLACEBO | | Apomorphine · HCl Sublingual Tablet | | | | | |
|---|---|---|---|---|---|---|---|---|---|
| | | | | 3 Mg Dose (μg/kg) | | 4 Mg Dose (μg/kg) | | 5 Mg Dose (μg/kg) | |
| Patient # | (Wt., kg) | Erotic #1 | Neutral #1 | Erotic #2 | Neutral #2 | Erotic #3 | Neutral #3 | Erotic #4 | Neutral #4 |
| 401 | (68.5) | 31 | 28 | 29 (44) | 27 (44) | 33 (58) | 27 (58) | | |
| 402 | (70.3) | 12 | 4 | 12 (43) | 4 (43) | 17 (57) | 6 (57) | | |
| 403 | (118) | 16 | 4 | 22* (25) | 5 (25) | 22* (34) | 25 (34) | | |
| 404 | (83.5) | 24 | 10 | 26* (36) | 17 (36) | 25* (48) | 17 (48) | | |
| 405 | (78) | 11 | 1 | 18* (38) | 6 (38) | 12 (51) | 8 (51) | 10 (64) | 5 (64) |
| 406 | (80) | 14 | 5 | 18* (38) | 17 (38) | 17* (50) | 2 (50) | | |
| 407 | (100) | 8 | 0 | 18* (30) | 4 (30) | 10 (40) | 3 (40) | | |
| 408 | (86.2) | 28 | 18 | 32 (35) | 21 (35) | 34 (46) | 22 (46) | | |
| 409 | (93) | 2 | 0 | 4 (32) | 1 (32) | 8 (43) | 6 (43) | 5 (54) | 4 (54) |
| 410 | (80) | 3 | 0 | 13 (38) | 16 (38) | 8 (50) | 7 (50) | | |
| 411 | (98) | 13 | 5 | 26* (31) | 23* (31) | 24* (42) | 20 (42) | | |
| 412 | (73) | 7 | 3 | 7 (41) | 1 (41) | 28* (55) | 19* (55) | | |

*Patients with score higher than 16 (see scoring table) are positive respondents.
Out of 12 patients who were treated in this study, 5 showed improvement at both 3 mg and 4 mg doses.
Two (2) showed response only at one dose.
No improvement in clinical response was observed at 5 mg dose.

The data of Pilot Study #4 were analyzed in two ways. First, mean erectile function was compared across placebo, 3 mg and 4 mg doses under two stimulus backgrounds, erotic and neutral. Next erectile function scores were dichotomized, with values less than sixteen considered to reflect erectile insufficiency.

A. Mean Erectile Function

Table VIII A shows means and standard errors for all three treatments under both backgrounds, erotic and neutral. Means were compared using a restricted maximum likelihood generalized linear model containing two main effects, treatment and stimulus, and the treatment by stimulus interaction. An appropriate variance-covariance structure was established for the underlying statistical model using Akaike's criterion. Table VIII B presents the statistical results for the main effects of treatment and of stimulus, for the treatment by stimulus interaction, and for orthogonal contrasts within the erotic and neutral conditions. It can be seen that the treatment main effect (i.e., general difference across treatment conditions without regard to stimulus background) is statistically significant; that the main effect of stimulus (i.e., general difference across stimulus backgrounds without regard to treatment) is statistically significant; and that the treatment by stimulus interaction is not statistically significant. These findings imply that active treatment is more effective than placebo and that this finding, although stronger when using an erotic stimulus, is true regardless of stimulus background (see FIG. 1). The orthogonal (statistically independent) contrasts confirm that active treatment is superior at a statistically significant level under both erotic and neutral conditions, but also indicate that the difference between the 3 mg and 4 mg dose does not exceed that expected by chance for the number of patients (12) used in this study.

B. Percent Successful Erectile Function

Figure 2:
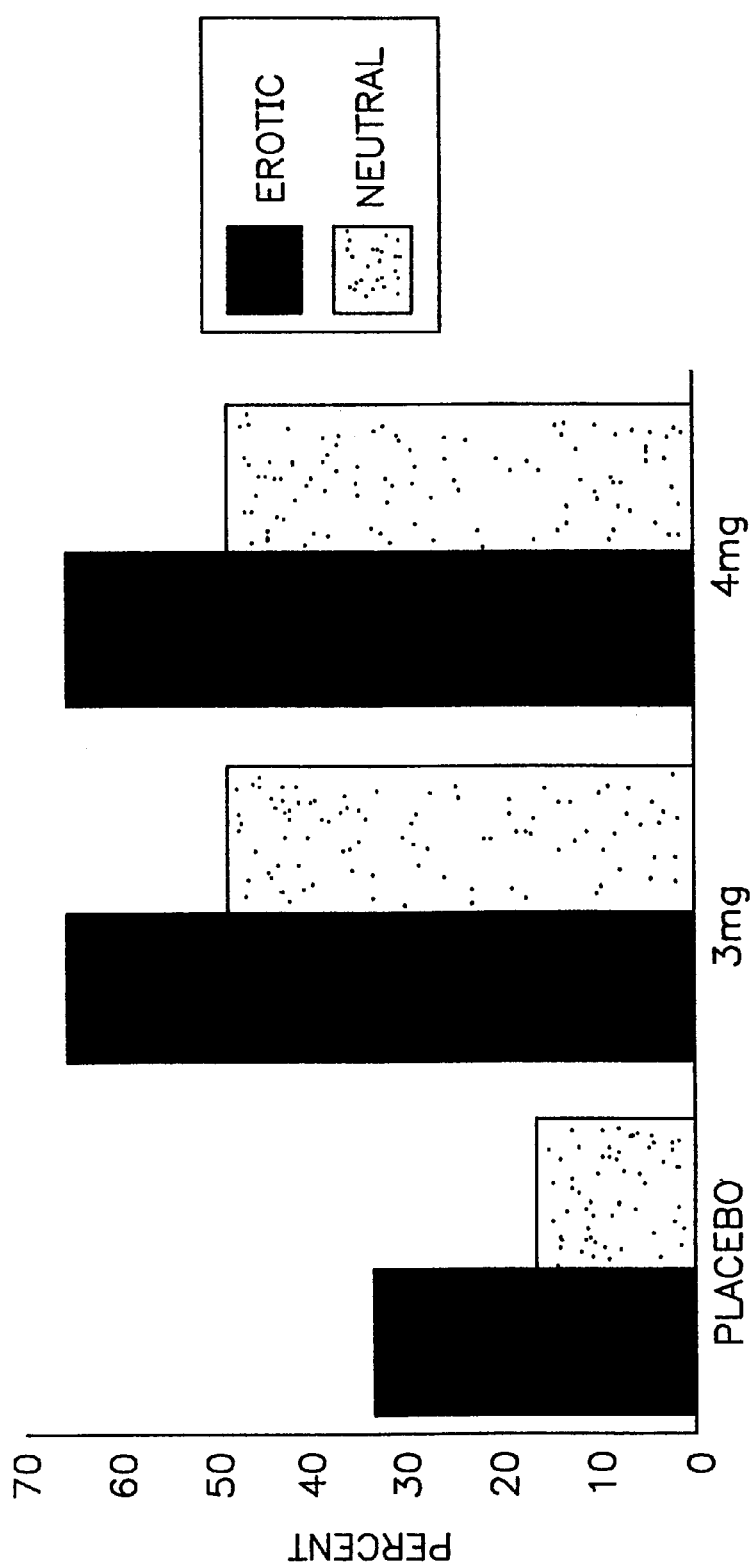
FIG. 2 is a bar graph depicting the percent successful erectile function for placebo, 3-milligram apomorphine dose, and 4-milligram apomorphine dose under erotic and neutral conditions.
Figure 3:
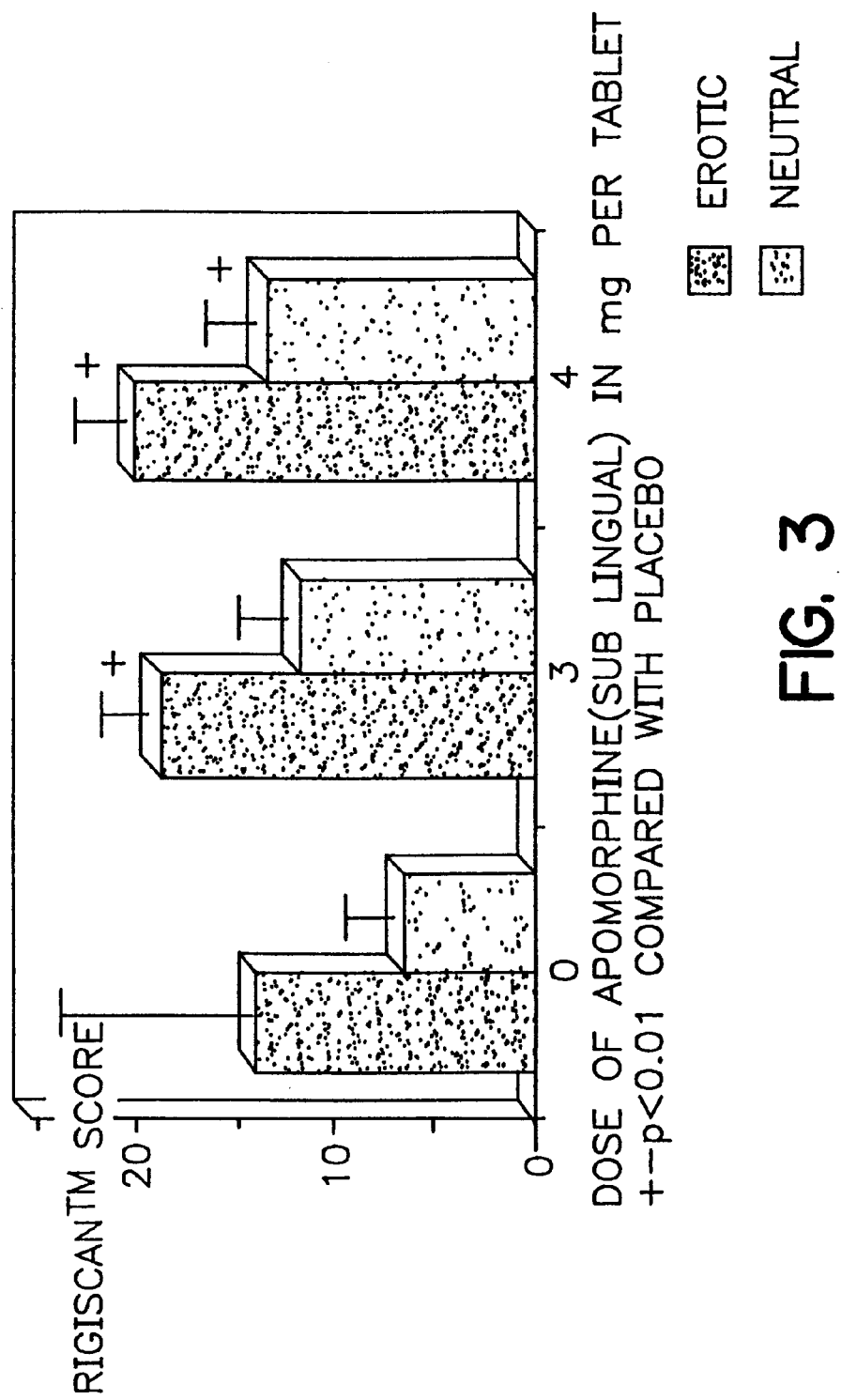
FIG. 3 is a bar graph presenting yet another comparison of erectile function noted in Pilot Study #4 in terms of RIGISCAN™ monitor score versus placebo, 3 milligrams of apomorphine and 4 milligrams of apomorphine under erotic and neutral conditions.

FIG. 2 and Table VIII C show that the statistically significant superiority of active over placebo treatment, regardless of stimulus background, is maintained when the erectile function scores are classified to reflect success (score at least 16) or failure (score less than 16).

TABLE VIII A

Mean and Percent Successful Erectile Function

| Stimulus | Treatment | N | Mean (SE) | Percent (SE) |
|---|---|---|---|---|
| Erotic | Placebo | 12 | 14.08 (2.69) | 33.33 (13.61) |
|  | 3 mg | 12 | 18.75 (2.51) | 66.67 (13.61) |
|  | 4 mg | 12 | 19.83 (2.67) | 66.67 (13.61) |
| Neutral | Placebo | 12 | 6.50 (2.45) | 16.67 (10.76) |
|  | 3 mg | 12 | 11.83 (2.68) | 50.00 (14.43) |
|  | 4 mg | 12 | 13.50 (2.61) | 50.00 (14.43) |

Note: Mean (SE) from SAS PROC UNIVARIATE. Percent (SE) from SAS PROC CATMOD.

TABLE VIII B

Anova for Mean Erectile Function

| EFFECT | DF | F | P-value |
|---|---|---|---|
| Treatment | 2.66 | 11.56 | 0.0000 |
| Stimulus | 1.66 | 37.14 | 0.0000 |
| Treatment by Stimulus | 2.66 | 0.10 | 0.9046 |

TABLE VIII B-continued

Anova for Mean Erectile Function

| EFFECT | DF | F | P-value |
|---|---|---|---|
| Contrasts |  |  |  |
| Erotic: Placebo vs. Treatment | 1.66 | 9.30 | 0.0033 |
| Erotic: 3 mg vs. 4 mg | 1.66 | 0.30 | 0.5849 |
| Neutral: Placebo vs. Treatment | 1.66 | 13.03 | 0.0006 |
| Neutral: 3 mg vs. 4 mg | 1.66 | 0.71 | 0.4014 |

Note: Restricted maximum likelihood analysis performed using SAS PROC MIXED.

TABLE VIII C

Logistic Regression for Percent Successful Erectile Function

| EFFECT | DF | $X^2$ | P-value |
|---|---|---|---|
| Treatment | 2 | 15.36 | 0.0005 |
| Stimulus | 1 | 5.14 | 0.0233 |
| Treatment by Stimulus | 2 | 0.00 | 1.0000 |
| Contrasts |  |  |  |
| Erotic: Placebo vs. Treatment | 1 | 9.60 | 0.0019 |
| Erotic: 3 mg vs. 4 mg | 1 | 0.00 | 1.0000 |
| Neutral: Placebo vs. Treatment | 1 | 9.60 | 0.0019 |
| Neutral: 3 mg vs. 4 mg | 1 | 0.00 | 1.0000 |

Note: Analysis performed using SAS PROC CATMOD.

TABLE IX

Visual Analogue Scale (VAS)
(to be completed by the patient)
Please mark each line clearly at the point which indicates how you are feeling right now.
Each line represents the full range of each feeling.
(There are no right or wrong answers)

Score (mm)

| 1. | Alert | Drowsy |  |
| 2. | Calm | Excited |  |
| 3. | Yawning | Not Yawning |  |
| 4. | Fuzzy | Clear Headed |  |
| 5. | Well Coordinated | Clumsy |  |
| 6. | Tired | Energetic |  |
| 7. | Contented | Disconnected |  |
| 8. | Troubled | Tranquil |  |
| 9. | Mentally slow | Quick Witted |  |
| 10. | Tense | Relaxed |  |
| 11. | Attentive | Dreamy |  |
| 12. | Stomach Upset | Feeling Well |  |
| 13. | Anxious | Carefree |  |

(measure from left to right)

Dose Evaluation Study

Clinical response to sublingual administration of apomorphine was evaluated utilizing a group of 60 non-vasculogenic impotent patients. Each patient had a history of erectile dysfunction for at least 3 months, normal biothesiometry response, and normal cavernosometry results.

The patients were divided into seven groups. Each group received a predetermined dosage of apomorphine for 20 days in the form of apomorphine hydrochloride tablets 20 minutes prior to intercourse. Seven different dosages were evaluated—3 mg, 4 mg, 5 mg, 6 mg, 7 mg, 8 mg and 10 mg The tablet constituents were those shown in Table I, above. Assessment of response was made on the basis of the patient's report of his experience. A response was deemed positive when the patient experienced an erection sufficiently rigid to effect penetration. Side effects such as nausea and/or vomiting, if present, were noted as well.

The results of this study are compiled in Table X, below.

TABLE X

Results of Dose Evaluation Study

| No. of Patients | Dosage, mg | Positive Responses No. | % | Nausea No. | % | Vomiting No. | % |
|---|---|---|---|---|---|---|---|
| 5 | 3 | 0 | 0 | 0 | 0 | 0 | 0 |
| 5 | 4 | 2 | 40 | 1 | 20 | 1 | 20 |
| 10 | 5 | 5 | 50 | 2 | 20 | 1 | 10 |
| 10 | 6 | 7 | 70 | 2 | 20 | 2 | 20 |
| 10 | 7 | 7 | 70 | 2 | 20 | 2 | 20 |
| 10 | 8 | 7 | 70 | 3 | 30 | 3 | 30 |
| 10 | 10 | 8 | 80 | 4 | 40 | 4 | 40 |

From the foregoing Table it can be seen that at a 4-mg dosage 40 percent of patients had a positive response, at a 5-mg dosage 50 percent of patients had a positive response, at 6-mg, 7-mg, and 8-mg dosages 70 percent of patients had a positive response and at a 10-mg dosage 80 percent of patients had a positive response. However, the incidence of side effects increased as well as the dosage was increased.

The aforesaid apomorphine dosage forms are also well suited for diagnosing male human patients suffering from male erectile dysfunction. For diagnostic purposes, at least about 3 milligrams of apomorphine are administered sublingually to the patient and the patient is exposed to a visual erotic stimulus, e.g., an erotic videotape, while the patient's response thereto is monitored. If deemed desirable for diagnostic purposes, up to about 10 milligrams of apomorphine can be administered to the patient.

In particular, the patient's maximum increase in penile circumference (preferably tip as well as basal) is determined and the patient's maximum penile rigidity (preferably tip as well as basal) is determined. The determined circumferential increase and rigidity values are then compared against a predetermined base value. Equivalent methods of determining tumescence and rigidity can also be utilized.

Pilot Study #5

A clinical study, "Absorption and pharmacokinetic evaluation of apomorphine after sublingual and intravenous routes of administration" compared the absorption and pharmacokinetic profile of apomorphine administered intravenously and slowly at a 1 mg dose with apomorphine sublingual tablets at doses of 4 mg (Table I) and 8 mg administered on 3 occasions, 4 days apart, over a 12 day period in a cross-over study design. The tolerance for apomorphine for each route and each dose administered was determined.

The study was conducted as an open-label, single center, 3-way crossover design. The study population was seven healthy, Caucasian male volunteers between 18 and 35 years of age. A 15-day pre-study evaluation period was followed by a 12-day active treatment phase. Three doses (one intravenous; 2 sublingual) were administered to each subject in random order 4 days apart. A total of 36 serum samples were obtained from each subject at the following time periods: 0, 2, 3, 5, 10, 20, 30 and 45 minutes; and 1, 2, 3, 4 and 6 hours post dose administration.

Safety was assessed within 15 days prior to study start and within one week after the last dose was administered. General physical examination was performed. Change from baseline in vital signs, height/weight measurements, ECG, orthostatic arterial pressures, heart rate, serum chemistry profile, hematology profile and urinalysis were recorded. Adverse experiences were recorded at each visit and tabulated.

Data Analysis

1. Pharmacokinetic Analysis

Pharmacokinetic analysis was performed by compartmental and noncompartmental methods described below. Nonlinear, iterative, least-squares regression analysis was performed with the computer program, PPHARM (Simed Co., Philadelphia, Pa.).

A. Compartmental Analysis

The apomorphine plasma concentration data for each subject following intravenous administration was fitted to two-compartment open model with a first order input function as described by the following equations.

Plasma apomorphine concentration was described for intravenous administration data by equation (1):

$$C_t = Ae^{-\alpha t} + Be^{-\beta t} \tag{1}$$

Plasma apomorphine concentration was described for sublingual tablet administration by equations (2) and (3):

$$C_t = \frac{FDk_a}{V_d(k_a - k_e)} \left( e^{-k_e(t-t_{lag})} - e^{-k_a(t-t_{lag})} \right) \tag{2}$$

$$C_t = Ae^{-\alpha(t-t_{lag})} + Be^{-\beta(t-t_{lag})} + Ce^{-k_a(t-t_{lag})} \tag{3}$$

In the above equations, $C_t$ is the apomorphine plasma concentration at time t; F is the relative bioavailability, which is assumed to be one for intravenous administration; $K_a$ is the first order rate constant for sublingual absorption; $K_e$ is the first order rate constant for elimination; $V_d$ is the volume of distribution; D is the apomorphine dose; t is time; $t_{lag}$ is the lag time before onset of sublingual absorption; A, B, C are the intercepts of the distribution, elimination, and absorption phases, respectively; $\alpha$ is the distribution rate constant; $\beta$ is the elimination rate constant; and $K_a$ is the absorption rate constant.

Initial estimates of the intravenous and sublingual pharmacokinetic parameters were obtained with the computer program PPHARM (Simed Co., Philadelphia, Pa.). These initial estimates were used to fit the data to equations (1), (2) and (3) by nonlinear iterative least squares regression analysis. The results are shown graphically in FIG. 4. The estimate of F (relative bioavailability) for sublingual administration was obtained from the noncompartmental analysis outlined below.

Visual inspection of the fitted curves, analysis of the residual plots, the Akaike information criterion, and correlation coefficients between observed and calculated values were used to select the appropriate pharmacokinetic model for each set of plasma concentration versus time data. A weighting factor was used to fit the data.

The regression analysis provided the final estimates of the pharmacokinetic parameters: $V_d$, $K_e$, $K_a$, and $t_{lag}$ from equation (2), and A, B, C, $\alpha$, $\beta$, $k_a$, and $t_{lag}$ from equation (3). The maximum plasma concentration ($C_{max}$), time to maximum plasma concentration ($T_{max}$), and $V_d$ (volume of distribution) were calculated using standard compartmental pharmacokinetic equations (Gibaldi, M. & Perrier, D. *Pharmacokinetics*, 2d edition, Marcel Dekker, Inc. New York, 1982).

The values for $C_{max}$ and $T_{max}$ obtained by visual inspection of the plasma concentration versus time curve were reported for comparative purposes. Model dependent and independent pharmacokinetic parameters (presented in Tables XI–XIV) were calculated for each patient using the best fit of Equation (3) to the data.

B. Noncompartmental Analysis:

$$F = \frac{AUC_{SL} * D_{IV}}{AUC_{IV} * D_{SL}} \quad (4)$$

2. Statistical Analysis:

An analysis of variance (ANOVA) for a three-way crossover study design was utilized to compare the pharmacokinetic parameters (AUC, $C_{max}$, and $t_{lag}$) determined as described above for the intravenous administration at 1 mg dose and those determined for the sublingual administration of apomorphine at the 4 mg and the 8 mg doses. The ANOVA was tested for the presence of any period or residual carryover effects in the data. Statistical significance was set at an alpha level equal to 0.05. The ability of the ANOVA to detect both a 20% difference and the observed difference between the sublingual and intravenous pharmacokinetic parameters was determined. In addition to the ANOVA, the 95% confidence interval of the percent difference between the sublingual and SC parameters was calculated from the error variance and degrees of freedom of the ANOVA model.

The data were summarized as the mean ± standard deviation in Tables XI–XIV below.

TABLE XI

NONCOMPARTMENTAL PHARMACOLOGIC PARAMETERS
(MEAN ± SD) AND RANGE

| Parameter | IV Administration | | | | 4 mg Dose | | | | 8 mg Dose | | | |
|---|---|---|---|---|---|---|---|---|---|---|---|---|
| | Mean | ±SD | Low | High | Mean | ±SD | Low | High | Mean | ±SD | Low | High |
| Ke (min$^{-1}$) | 0.0237 | 0.0140 | 0.0091 | 0.0432 | 0.0156 | 0.0138 | 0.0038 | 0.0336 | 0.0056 | 0.0036 | 0.00222 | 0.0102 |
| T½(min) | 39.44 | 0.219 | 16.04 | 76.49 | 89.18 | 75.43 | 20.62 | 183.60 | 176.30 | 112.30 | 68.09 | 314.6 |
| Tmax (min) | 2.286 | 1.254 | 1.000 | 5.000 | 17.50 | 18.48 | 5.000 | 45.00 | 52.50 | 85.10 | 5.000 | 15.00 |
| Cmax (min) | 8.364 | 3.886 | 3.400 | 12.90 | 0.8375 | 0.6848 | 0.3000 | 0.8500 | 2.069 | 2.366 | 0.5750 | 1.150 |
| AUC (0-Inf) (min*ng/ml) | 206.9 | 45.47 | 140.8 | 260.1 | 31.64 | 18.62 | 10.13 | 55.55 | 339.9 | 459.2 | 15.00 | 316.6 |
| Cl (ml/min) | 0.0051 | 0.0012 | 0.0038 | 0.0071 | 0.0456 | 0.0361 | 0.0180 | 0.0988 | 0.2056 | 0.2460 | 0.0253 | 0.5333 |
| Vd (beta) (ml) | 0.2344 | 0.1532 | 0.0056 | 0.4982 | 4.076 | 2.053 | 1.017 | 5.277 | 69.09 | 115.80 | 7.932 | 64.27 |
| Vd (SS) (ml) | 0.1942 | 0.0817 | 0.1357 | 0.3401 | 1.836 | 0.7112 | 0.999 | 2.475 | 46.30 | 74.46 | 6.523 | 12.42 |
| MRT (min) | 40.29 | 18.90 | 20.14 | 75.32 | 64.25 | 55.14 | 15.12 | 137.5 | 143.7 | 148.0 | 23.29 | 329.3 |
| F* (% Relative Bioavailability) | — | — | | | 0.04 | (4.0%) | | | 0.21 | (21%) | | |
| F* = (AUC$_{SL}$*DOSE$_{IV}$)/(AUC$_{IV}$*DOSE$_{SL}$) | | | | | | | | | | | | |

Cl = clearance
Vd = volume of distribution @ $\beta$ stage.
Vd (SS) = volume of distribution steady state
MRT = means residual time The area under the curve, $AUC_{0-inf}$, was determined by adding the $AUC_{0-last}$ to the $AUC_{t-last}$, where $AUC_{t-last}=C_t/R_e$, $C_t$ is the plasma concentration at time $^t$, and $R_e$ is $K_e$, the first order rate constant for elimination.

If the plasma concentration versus time data for a subject could not be adequately fit to equation (1), (2) or (3), the $K_e$ was determined by linear regression analysis of the log plasma concentration versus time during the post-absorption phase. Estimates of noncompartmental parameters $C_{max}$ and $T_{max}$ were obtained from visual inspection of the plasma concentration time curves.

The relative bioavailability (F) for a sublingual dose was calculated by the following equation:

TABLE XII

Noncompartmental Pharmacokinetic Parameters (Mean ± SD) for IV Administration (1 mg)
n = 7

| | Subject | | | | Subject | | | Range | | | |
|---|---|---|---|---|---|---|---|---|---|---|---|
| | #1 | #2 | #3 | #4 | #5 | #6 | #7 | Mean | ±SD | Low | High |
| Ke (/min) | 0.0432 | 0.0129 | 0.0091 | 0.0419 | 0.0168 | 0.0150 | 0.0268 | 0.0237 | 0.0140 | 0.0091 | 0.0432 |
| T½(min) | 16.04 | 53.79 | 76.49 | 16.56 | 41.22 | 46.18 | 25.84 | 39.44 | 21.92 | 16.04 | 76.49 |
| Tmax (min) | 2.000 | 2.000 | 2.000 | 2.000 | 2.000 | 5.000 | 1.000 | 2.286 | 1.254 | 1.000 | 5.000 |
| Cmax (min) | 8.400 | 11.200 | 4.150 | 12.250 | 12.900 | 3.400 | 6.250 | 8.364 | 3.886 | 3.400 | 12.900 |
| AUC (0-Inf) (min*ng/ml) | 140.8 | 255.4 | 221.5 | 177.1 | 224.6 | 169.0 | 260.1 | 206.9 | 45.47 | 140.8 | 260.1 |
| Cl (ml/min) | 0.0071 | 0.0039 | 0.0045 | 0.0056 | 0.0045 | 0.0059 | 0.0038 | 0.0051 | 0.0012 | 0.0038 | 0.0071 |
| Vd (beta) (ml) | 0.1643 | 0.3039 | 0.4982 | 0.0056 | 0.2648 | 0.2574 | 0.1466 | 0.2344 | 0.1532 | 0.0056 | 0.4982 |
| Vd (SS) (ml) | 0.1430 | 0.1512 | 0.3401 | 0.1147 | 0.2174 | 0.2574 | 0.1357 | 0.1942 | 0.0817 | 0.1357 | 0.3401 |
| MRT (min) | 20.14 | 38.62 | 75.32 | 20.32 | 48.82 | 43.50 | 35.31 | 40.29 | 18.90 | 20.14 | 75.32 |

TABLE XIII

Noncompartmental Pharmacokinetic Parameters (Mean ± SD)
for Sublingual Administration (4 mg Dose)
n = 4

| | Subjects | | | | Range | | | |
|---|---|---|---|---|---|---|---|---|
| | #1 | #3 | #6 | #7 | Mean | ±SD | Low | High |
| Ke (/min) | 0.0188 | 0.0336 | 0.0060 | 0.0038 | 0.0156 | 0.0138 | 0.0038 | 0.0336 |
| T½(min) | 36.78 | 20.62 | 115.7 | 183.6 | 89.18 | 75.43 | 20.62 | 183.6 |
| Tmax (min) | 10.00 | 10.00 | 5.000 | 45.00 | 17.50 | 18.48 | 5.000 | 45.00 |
| Cmax (ng/ml) | 0.8500 | 1.8000 | 0.3000 | 0.4000 | 0.8375 | 0.6848 | 0.3000 | 0.8500 |
| AUC (0-Inf) (min*ng/ml) | 10.13 | 29.25 | 31.64 | 55.55 | 31.64 | 18.62 | 10.13 | 55.55 |
| Cl (ml/min) | 0.0988 | 0.0342 | 0.0316 | 0.0180 | 0.0456 | 0.0361 | 0.0180 | 0.0988 |
| Vd (beta) (ml) | 5.241 | 1.017 | 5.277 | 4.769 | 4.076 | 2.053 | 1.017 | 5.277 |
| Vd (SS) (ml) | 1.494 | 0.999 | 2.377 | 2.475 | 1.836 | 0.7112 | 0.999 | 2.475 |
| MRT (min) | 15.12 | 29.23 | 75.19 | 137.47 | 64.25 | 55.14 | 15.12 | 137.47 |

TABLE XIV

Noncompartmental Pharmacokinetic Parameters (Mean ± SD)
for Sublingual Administration (8 mg Dose)
n = 4

| | Subjects | | | | Range | | | |
|---|---|---|---|---|---|---|---|---|
| | #2 | #3 | #4 | #6 | Mean | ±SD | Low | High |
| Ke (/min) | 0.0067 | 0.0032 | 0.0120 | 0.0022 | 0.0056 | 0.0036 | 0.0022 | 0.0102 |
| T½(min) | 104.0 | 218.4 | 68.09 | 314.6 | 176.3 | 112.3 | 68.09 | 314.6 |
| Tmax (min) | 180.0 | 10.00 | 15.00 | 5.000 | 52.50 | 85.10 | 5.000 | 180.0 |
| Cmax (ng/ml) | 5.600 | 1.150 | 0.9500 | 0.5750 | 2.069 | 2.366 | 0.5750 | 5.600 |
| AUC (0-Inf) (min*ng/ml) | 996.6 | 316.6 | 31.25 | 15.00 | 339.9 | 459.2 | 15.00 | 996.6 |
| Cl (ml/min) | 0.008 | 0.0253 | 0.2560 | 0.5333 | 0.2056 | 0.2460 | 0.008 | 0.5333 |
| Vd (beta) (ml) | 1.204 | 7.932 | 25.15 | 242.1 | 69.09 | 115.8 | 1.204 | 242.1 |
| Vd (SS) (ml) | 157.9 | 8.320 | 6.523 | 12.42 | 46.30 | 74.46 | 6.523 | 157.9 |
| MRT (min) | 196.7 | 329.3 | 25.48 | 23.29 | 143.7 | 148.0 | 23.29 | 329.3 |

TABLE XV

Summary of Pharmacokinetic Parameters for Apomorphine HCl in Humans

| | THIS STUDY | | | Durif, F. et al., Clin. Neuropharm. 16:157–166 (1933) | | Gancher, S.T., et al. Movement Disorders 6:212–216 (1991). | | | Montastruc, J.L., et al. Clin. Neuropharmacol. 14:432–437 (1991). | |
|---|---|---|---|---|---|---|---|---|---|---|
| ROUTE | i.v. | s.l. | s.l. | s.l. | s.l. | s.l. | s.c. | i.v. | s.l. | s.c. |
| # Subjects | 7 | 7 | 7 | 7 | 7 | 5 | 5 | 5 | 9 | 9 |
| # Tablets x Strength (mg) | n/d | 1 × 4 | 1 × 8 | 7 × 3 | 14 × 3 | 3 × 6 | n/a | n/a | 10 × 3 | n/a |
| Dose (mg/kg) | 0.01 | 0.06 | 0.114 | 0.3 | 0.6 | 0.25 | 0.02 | 0.038 | 0.42 | 0.04 |
| $C_{max}$ (ng/ml) | 8.3 | 0.83 | 2.07 | 7.5 | 22.7 | 14.3 | 19.36 | 31.2 | 28 | 26 |
| $T_{max}$ (min) | 2.2 | 17.5 | 52.5 | 31.5 | 38.3 | 45 | 6.5 | 6.7 | 41 | 18 |
| AUC (min*ng/ml) | 207 | 31.6 | 340 | 929 | 2,277 | 1,057 | 592.7 | 881.1 | 1,882 | 837 |
| Cl (l/hr/kg) | 4.37 | n/d | n/d | 2.1 | 1.8 | n/d | n/d | n/d | n/d | n/d |
| Vd (l/kg) | 3.35 | 2.33 | 2.07 | 3.4 | 2.8 | n/d | n/d | 0.043* | n/d | n/d |
| MRT (min) | 40.3 | 64.2 | 143.7 | 128 | 125 | n/d | n/d | n/d | n/d | n/d |
| $T_{½}$(min) | 39.4 | 89.2 | 176.3 | 72 | 70 | n/d | n/d | n/d | n/d | n/d |
| Bioavailability (F) | n/a | 4% | 21% | 10% | 10% | 17% | n/a | n/a | n/d | n/a | n/d = not done
n/a = not applicable
*Calculated
Clin. Neuropharm. 16:157–166 (1993)

Figure 4:
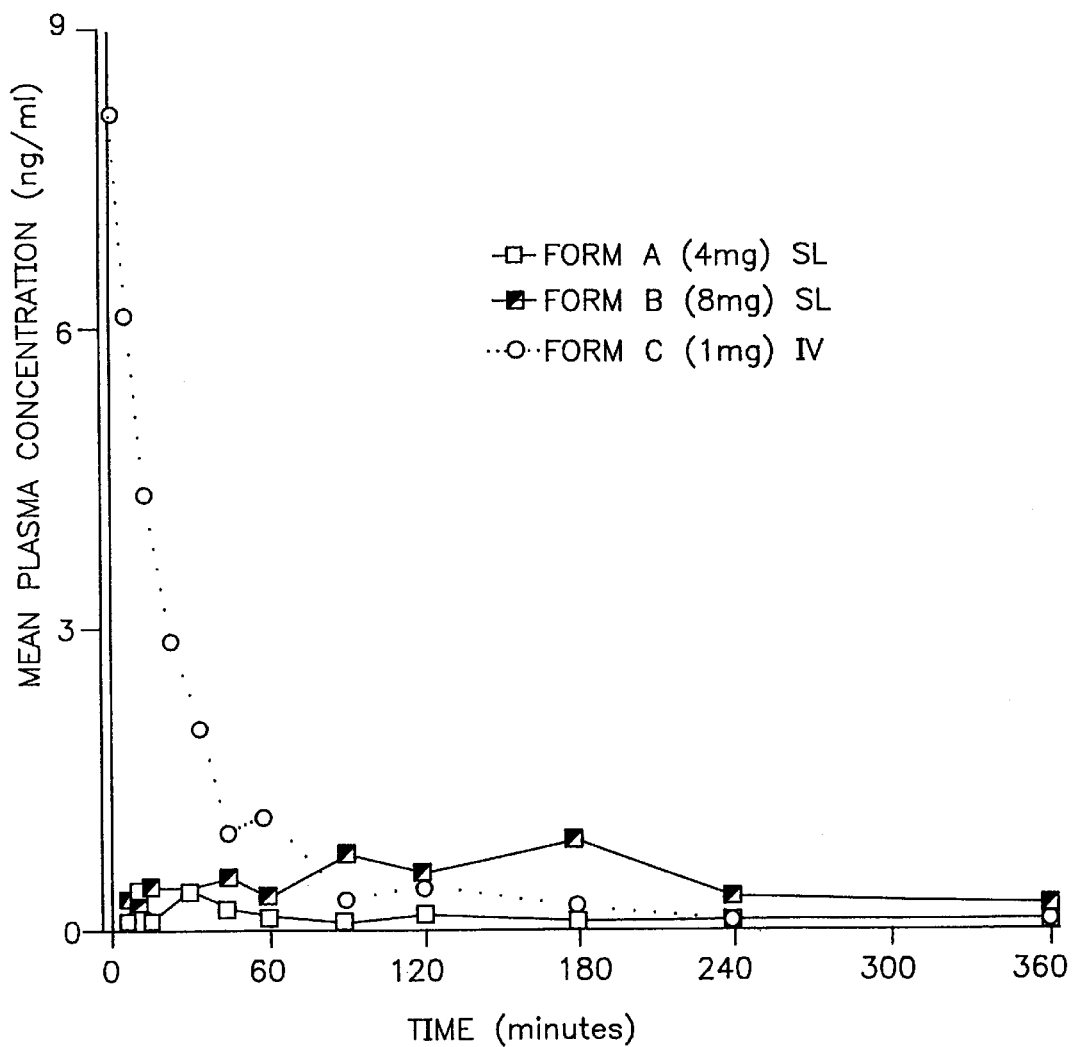
FIG. 4 is a graphical representation of a comparison of the plasma concentration time profiles of apomorphine after intravenous administration at a dose of 1 mg (open circles, n=7), sublingual administration at a dose of 4 mg (open squares, n=4) and sublingual administration at a dose of 8 mg (half-filled squares, n=4).

The results, summarized in Tables XI–XIV above and shown graphically in FIG. 4, show that the plasma concentration of apomorphine drops quickly when the drug is administered intravenously. In contrast, the plasma concentration of apomorphine rises slowly to a lower level when administered sublingually.

The importance of these findings is put into perspective when compared to information on the administration of apomorphine that is available in the literature (Table XV). The sublingual administration of apomorphine by the present invention produced a lower plasma concentration than the administration and dosage regimes listed for previous reports.

Pilot Study #6

A clinical study of patient tolerance of escalating doses in sublingual tablet administration of APO for the treatment of psychogenic male erectile dysfunction was performed. The pilot study compared the effects of sublingual tablet administration of placebo, and 4, 6 and 8 mg apomorphine hydrochloride (APO) on male erectile dysfunction as measured by Rigiscan™ monitoring and self-reported satisfaction with the treatment results.

The study included 50 men with psychogenic male erectile dysfunction (MED). The study was conducted in three phases. In the first phase, the subject's penile erectile response (measured with the Rigiscan™ ambulatory tumescence monitor) was evaluated. The subject received a placebo tablet for sublingual administration and then viewed a 30-minute video consisting of two 10-minute erotic sequences separated by a 10-minute neutral sequence. Subjects completed a visual analogue scale questionnaire (VAS, Table VI) about their feelings and well-being.

In the second phase, subjects returned to the clinic for four visits, each visit one week apart. Subjects received one sublingual administration of either placebo, or 4, 6 and 8 mg APO at each visit. Doses of APO were administered in ascending order with the placebo being randomly assigned for use at one of the four visits. The procedures performed before and after drug administration were the same as those in the first phase. After completion of the fourth visit, the investigator determined for each subject the most effective and well-tolerated APO dose for home use in the third phase of the study.

The third phase, a home-use phase, lasted 5 weeks. During this phase, subjects attempted coitus at least once each week after taking a single APO tablet. After each attempt the subject and his partner completed a Sexual Function questionnaire (Table XVI). Subjects had a final evaluation at the end of the 5-week, home-use phase.

Fifty males with psychogenic MED were enrolled in this three phase trial. The first aim of this study was to determine the safety and tolerance of APO in the treatment of MED. Several adverse events directly linked with administration of APO in humans were expected: yawning, nausea, vomiting, and cardiovascular effects. Indeed, nausea was the primary adverse event reported in this trial with an overall incidence of less than 13% of the subjects for all administered doses and only two cases were considered severe. The incidence of vomiting was less than 3% for all administered doses.

Hypotension was reported as an adverse event in some subjects in this study, along with bradycardia, dizziness, syncope, and pallor. Only single cases of hypotension and pallor were judged severe in this study. Increased sweating and fatigue were also reported. One of the cases of increased sweating was considered severe. The other severe adverse events (mouth edema, dysphagia, upper respiratory tract infection) were judged unrelated to treatment.

Changes in the serum chemistry values and vital signs paralleled the adverse event reports. There were no clinically significant changes except for one subject judged to have abnormal liver function of unknown origin. There were no clinically significant changes in the blood or urinalysis values due to drug.

The efficacy of APO was evaluated during the first two phases of the study in which subjects were attached to the Rigiscan™ monitor. Subjects were initially treated with placebo in the first phase. In the second phase, patients received 4, 6 and 8 mg APO tablets with a placebo tablet randomly interspersed in the treatment.

There were highly significant effects of APO treatment compared to placebo. These observations indicate that APO has effects on penile function in both erotic and neutral environments (Tables XVII–XIX). All summed scores showed significant treatment effects at one or more of the three doses of APO. The overall Rigiscan™ score results were significant to highly significant for a treatment effect of 4, 6 and 8 mg compared to the initial placebo. In addition, most of the treatment effects were significant to highly significant compared to the second placebo.

The effects in the erotic video sequences were larger than the effects in the neutral video sequence (TABLES XVII–XIX). Effects in erotic video sequence one were larger than the effects in erotic video sequence two (TABLE XVII). More significant treatment effects were seen in response to the neutral video sequence, but this reflects the larger number of subjects in this data subset, as one center did not show the erotic video sequences. All doses of APO were effective in causing erections (Rigiscan™ reading ≧15 in the presence of erotic stimulation; TABLE XVII).

During the third phase, subjects had recorded at baseline, their satisfaction, erection, number of attempts, and successful intercourse on a VAS scale. Evaluable subjects first recorded a success rate, then completed VAS for erection results and satisfaction with intercourse following take-home treatment. Success rate was calculated for mg as well as $\mu$g/kg body weight doses (males). Several evaluations of the data were made including the male and female responses to treatments. The overall average success rate is 69% with APO treatment which is much higher than the average baseline rate 28% (Tables XX, XX1).

The success rate showed numerical increase at tablet strength from 4 mg to 6 mg, but a decrease at 8 mg (TABLE XX). The highest success rate was 73% in both males and females at a tablet strength of 6 mg (TABLE XX). When the dosage is examined as a function of body weight, a dosage range of 50–74 $\mu$g/kg gave the highest success rate(: 82%) in females and (80%) in males (Table XXI). The dosage range of 35–50 $\mu$g/kg gave the highest success rate.

The optimal response was observed with 4 or 6 mg APO sublingual tablets which caused erections in the majority (72%) of men with male erectile dysfunction (MED) with few severe adverse effects.

TABLE XVI

SEXUAL FUNCTION STUDY HOME QUESTIONNAIRE - Male
Please answer questions within 12–24 hours of taking sublingual tablet.

Initials:_____ Subject #:_____ Today's Date:_____ Time:_____
Date Table Taken:_____ Time:_____

The lines below represent the full range of feeling or response. Please mark each line clearly with a vertical (straight up and down) stroke at the point which represents your response. (There are no right or wrong answers. Do not write in boxes on right.)

1. What was your erection result after taking the sublingual tablet?

No Erection _____ Rigid Erection Suitable for Penetration [ ]

2. Did you have intercourse with wife/partner after taking tablet?   [ ] Yes   [ ] No
   IF NO, please circle all   0 - No erection.
   reasons that apply:   1 - Erection not sufficient for penetration.
   2 - Felt sick after after taking tablet. (Describe below in #4.)
   3 - I decided not to participate in intercourse.
   4 - Wife/partner decided not to participate.
   5 - Unrelated interruption (example, telephone call).
   6 - Wife/partner menstruating.
   7 - Other, explain: _____

3. What was your level of satisfaction with this attempt at sexual intercourse?
   Extremely Unsatisfied _____ Extremely Satisfied [ ]

4. Please describe any adverse reactions you experienced after taking the sublingual tablet. (Indicate when the reaction started and stopped, and any intervention taken i.e. "nosebleed on 5/1/94, used a cold compress".)

_____
   _____

5. Other comments? _____
   _____

TABLE XVII

Total Rigiscan Scores by Phase
Mean ± SEM
Phase II

| Video | Placebo 1 | Placebo 2 | 4 mg | 6 mg | 8 mg |
|---|---|---|---|---|---|
| | Phase I | | Phase II | | |
| Erotic 1<br>N = 31–36 | 11.44 ± 1.77 | 13.38 ± 2.05 | 15.31 ± 1.76* | 17.09 ± 1.64** | 19.84 ± 1.61** |
| Erotic 2<br>N = 29–36 | 11.39 ± 1.70 | 13.31 ± 1.88 | 15.26 ± 1.72* | 16.44 ± 1.98* | 17.79 ± 1.96** |
| Neutral<br>N = 41–48 | 7.98 ± 1.24 | 7.49 ± 1.26 | 11.11 ± 1.30** | 12.76 ± 1.12** | 11.98 ± 1.37** |
| | | Corresponding p-values (placebl 1/placebo 2) | | | |
| Erotic 1 | — | 0.3274 | 0.0120 | 0.0007 | 0.0001 |
| | — | — | 0.1405 | 0.0166 | 0.0005 |
| Erotic 2 | — | 0.4013 | 0.0276 | 0.0196 | 0.0007 |
| | — | — | 0.1907 | 0.1365 | 0.0091 |
| Neutral | — | 0.6243 | 0.0230 | 0.0009 | 0.0060 |
| | — | — | 0.0074 | 0.0002 | 0.0017 |

*Significantly higher than placebo 1
**Significantly higher than placebo 1 and placebo 2

TABLE XVIII

Penile Measurements (Maximum Increases Measured by Rigiscan ™). Erotic Video Sequence #1
Repeated Measures Analysis of Variance

| | | DESCRIPTIVE STATISTICS | | | ADJUSTED (LS) MEAN | | ANALYSIS OF VARIANCE | | |
|---|---|---|---|---|---|---|---|---|---|
| Site | Treatment | N | MEAN | SEM | LSMEAN | SEM | Source | p-value | |
| ALL SITES | Placebo #1 | 36 | 11.44 | 1.770 | 12.22 | 1.666 | Treatment | 0.0001 | * |
| | Placebo #2 | 32 | 13.38 | 2.051 | 13.65 | 1.714 | Site | 0.0264 | * |
| | 4 mg | 35 | 15.31 | 1.761 | 15.80 | 1.674 | Treatment by Site | 0.0595 | |
| | 6 mg | 34 | 17.09 | 1.841 | 17.20 | 1.695 | 4 mg vs Placebo #1 | 0.0120 | * |
| | 8 mg | 31 | 19.84 | 1.610 | 19.11 | 1.745 | 6 mg vs Placebo #1 | 0.0007 | * |
| SITE #1 | ALL TREATMENTS | 11 | 10.76 | 2.372 | 11.04 | 2.498 | 8 mg vs Placebo #1 | 0.0001 | * |
| | Placebo #1 | 11 | 9.73 | 2.854 | 9.73 | 2.931 | 4 mg vs Placebo #2 | 0.1504 | |
| | Placebo #2 | 10 | 9.00 | 3.300 | 9.21 | 2.996 | 6 mg vs Placebo #2 | 0.0166 | * |
| | 4 mg | 11 | 8.09 | 2.410 | 8.09 | 2.931 | 8 mg vs Ptacebo #2 | 0.0005 | * |
| | 6 mg | 11 | 10.82 | 3.065 | 10.82 | 2.931 | Placebo #1 vs. #2 | 0.3274 | |
| | 8 mg | 9 | 17.89 | 2.988 | 17.36 | 3.070 | | | |
| SITE #2 | ALL TREATMENTS | 16 | 13.89 | 1.942 | 14.25 | 2.083 | | | |
| | Placebo #1 | 16 | 8.94 | 2.233 | 8.94 | 2.430 | | | |
| | Placebo #2 | 14 | 11.71 | 2.768 | 11.38 | 2.515 | | | |
| | 4 mg | 15 | 15.27 | 2.379 | 15.10 | 2.476 | | | |
| | 6 mg | 15 | 17.60 | 2.267 | 17.43 | 2.476 | | | |
| | 8 mg | 15 | 18.60 | 2.265 | 18.43 | 2.476 | | | |
| SITE #4 | ALL TREATMENTS | 9 | 21.21 | 3.437 | 21.49 | 2.776 | | | |
| | Placebo #1 | 9 | 18.00 | 4.304 | 18.00 | 3.240 | | | |
| | Placebo #2 | 8 | 21.75 | 4.242 | 20.36 | 3.337 | | | |
| | 4 mg | 9 | 24.22 | 2.837 | 24.22 | 3.240 | | | |
| | 6 mg | 8 | 24.75 | 3.740 | 23.36 | 3.337 | | | |
| | 8 mg | 7 | 25.00 | 3.259 | 21.52 | 3.444 | | | |

TABLE XIX

Penile Measurements (Maximum Increases Measured by Rigiscan ™). Neutral Video Sequence
Repeated Measures Analysis of Variance

| | | DESCRIPTIVE STATISTICS | | | ADJUSTED (LS) MEAN | | ANALYSIS OF VARIANCE | | |
|---|---|---|---|---|---|---|---|---|---|
| Site | Treatment | N | MEAN | SEM | LSMEAN | SEM | Source | p-value | |
| ALL SITES | Placebo #1 | 48 | 7.98 | 1.236 | 8.34 | 1.220 | Treatment | 0.0002 | * |
| | Placebo #2 | 43 | 7.49 | 1.257 | 7.65 | 1.272 | Site | 0.1092 | |
| | 4 mg | 47 | 11.11 | 1.295 | 11.47 | 1.226 | Treatment by Site | 0.7176 | |
| | 6 mg | 45 | 12.76 | 1.116 | 13.10 | 1.268 | 4 mg vs Placebo #1 | 0.0230 | * |
| | 8 mg | 41 | 11.98 | 1.366 | 12.40 | 1.331 | 6 mg vs Placebo #1 | 0.0009 | * |

TABLE XIX-continued

Penile Measurements (Maximum Increases Measured by Rigiscan ™). Neutral Video Sequence
Repeated Measures Analysis of Variance

| Site | Treatment | N | DESCRIPTIVE STATISTICS | | ADJUSTED (LS) MEAN | | ANALYSIS OF VARIANCE | | |
|---|---|---|---|---|---|---|---|---|---|
| | | | MEAN | SEM | LSMEAN | SEM | Source | p-value | |
| SITE #1 | ALL TREATMENTS | 11 | 10.56 | 1.987 | 10.70 | 1.789 | 8 mg vs Placebo #1 | 0.0060 | * |
| | Placebo #1 | 11 | 8.91 | 2.470 | 8.91 | 2.494 | 4 mg vs Placebo #2 | 0.0074 | * |
| | Placebo #2 | 10 | 5.60 | 2.574 | 5.68 | 2.587 | 6 mg vs Placebo #2 | 0.0002 | * |
| | 4 mg | 11 | 10.45 | 1.965 | 10.45 | 2.494 | 8 mg vs Placebo #2 | 0.0017 | * |
| | 6 mg | 11 | 12.73 | 2.832 | 12.73 | 2.494 | Placebo #1 vs. #2 | 0.6243 | |
| | 8 mg | 9 | 16.22 | 3.099 | 15.73 | 2.692 | | | |
| SITE #2 | ALL TREATMENTS | 16 | 7.02 | 1.192 | 7.22 | 1.495 | | | |
| | Placebo #1 | 16 | 4.44 | 1.554 | 4.44 | 2.068 | | | |
| | Placebo #2 | 14 | 5.86 | 2.099 | 5.71 | 2.182 | | | |
| | 4 mg | 15 | 8.73 | 2.610 | 8.70 | 2.126 | | | |
| | 6 mg | 15 | 9.60 | 1.514 | 9.56 | 2.126 | | | |
| | 8 mg | 15 | 7.73 | 1.694 | 7.70 | 2.126 | | | |
| SITE #3 | ALL TREATMENTS | 12 | 12.22 | 1.476 | 12.09 | 1.706 | | | |
| | Placebo #1 | 12 | 11.33 | 2.244 | 11.33 | 2.388 | | | |
| | Placebo #2 | 11 | 10.00 | 1.902 | 10.61 | 2.469 | | | |
| | 4 mg | 12 | 11.83 | 2.564 | 11.83 | 2.388 | | | |
| | 6 mg | 12 | 13.58 | 1.794 | 13.58 | 2.388 | | | |
| | 8 mg | 11 | 12.45 | 2.458 | 13.07 | 2.469 | | | |
| SITE #4 | ALL TREATMENTS | 9 | 11.63 | 2.864 | 12.35 | 2.023 | | | |
| | Placebo #1 | 9 | 8.67 | 4.052 | 8.67 | 2.758 | | | |
| | Placebo #2 | 8 | 9.25 | 3.990 | 8.58 | 2.891 | | | |
| | 4 mg | 9 | 14.89 | 3.071 | 14.89 | 2.758 | | | |
| | 6 mg | 7 | 18.14 | 2.747 | 16.51 | 3.046 | | | |
| | 8 mg | 6 | 15.33 | 4.462 | 13.11 | 3.236 | | | |

TABLE XX

Reported Success by Tablet Strength

| Group | 4 mg | 6 mg | 8 mg | Overall |
|---|---|---|---|---|
| Female | 5/7 (71.4%) | 11/15 (73.3%) | 4/7 (57.1%) | 20/29 (69.0%) |
| Male | 5/7 (71.4%) | 11/15 (73.3%) | 4/7 (57.1%) | 20/29 (69.0%) |

TABLE XXI

Reported Success by Apomorphine Dosage (μg/kg)

| Group | 35–50 μg/kg | 50–74 μg/kg | >74 μg/kg | Overall |
|---|---|---|---|---|
| Female | 3/5 (60.0%) | 9/11 (81.8%) | 8/13 (61.5%) | 20/29 (69.0%) |
| Male | 4/5 (80.0%) | 8/11 (72.7%) | 8/13 (61.5%) | 20/29 (69.0%) |

Subject Evaluabillty Rules for Take-home Part
1. Subjects who get one out of two successful intercourse is considered a success [based on subject's answers to the take-home questionaaires].
2. Subjects who tried the study medication at home, for at least two times.
3. Subjects who attempted to try a lower or higher does if the original take-home does did not produce optimum results in combination with anti-nausea agents.
4. Subjects [and partners] who filled out and returned take-home questionnaires.

The foregoing discussion and the reported studies are intended as illustrative of the present invention and are not to be taken as limiting. Still other variants within the spirit and scope of this invention are possible and will readily present themselves to those skilled in the art.

What is claimed is:

1. A sublingual controlled release apomorphine dosage form that maintains circulating serum and midbrain tissue levels of apomorphine within a range so as to induce an erection adequate for vaginal penetration but so as not to induce substantial nausea, said dosage form containing apomorphine, mannitol, ascorbic acid, citric acid, and magnesium stearate.

2. The dosage form in accordance with claim 1 additionally containing a β-cyclodextrin.

3. The dosage form in accordance with claim 2 wherein the β-cyclodextrin is hydroxypropyl-β-cyclodextrin.

* * * * *